United States Patent [19]

Omichinski et al.

[11] Patent Number: 5,081,584

[45] Date of Patent: Jan. 14, 1992

[54] COMPUTER-ASSISTED DESIGN OF ANTI-PEPTIDES BASED ON THE AMINO ACID SEQUENCE OF A TARGET PEPTIDE

[75] Inventors: James G. Omichinski, Potomac, Md.; Giorgio Fassina, Padova, Italy; Arthur D. Olson, Silver Spring; Snorri S. Thorgeirsson, Bethesda, both of Md.

[73] Assignee: United States of America, Washington, D.C.

[21] Appl. No.: 322,266

[22] Filed: Mar. 13, 1989

[51] Int. Cl.$^5$ .................. G06F 15/42; G01N 33/68
[52] U.S. Cl. .................. 364/497; 364/496; 435/69.1; 436/89; 935/78; 935/87
[58] Field of Search .................. 364/496, 497, 413.01; 435/69.1, 68.1, 69.4; 436/508, 89; 935/77, 78, 87

[56] References Cited

U.S. PATENT DOCUMENTS

| | | | |
|---|---|---|---|
| 4,849,077 | 7/1989 | Rosenthal et al. | 935/77 |
| 4,849,352 | 7/1989 | Sullivan et al. | 435/68.1 |
| 4,853,871 | 8/1989 | Pantoliano et al. | 364/496 |
| 4,863,849 | 9/1989 | Melamede | 935/78 |
| 4,863,857 | 9/1989 | Blalock et al. | 435/69.1 |
| 4,881,175 | 11/1989 | Ladner | 364/496 |
| 4,902,783 | 2/1990 | Goda et al. | 435/69.1 |
| 4,8001,166 | 1/1989 | Horn et al. | 935/87 |

OTHER PUBLICATIONS

Bost et al., "Similarity Between the Corticotropin (ACTH) Receptor and a Peptide Encoded by an RNA that is Complementary to ACTH mRNA" Mar. 1985, pp. 1372–1375.

Brentani et al., "Characterization of the Cellular Receptor for Fibronectin through a Hydropathic Complementarity Approach", Jan., 1988, pp. 364–367.

Elton et al., "Purification of an Angiotensin II Binding Protein by Using Antibodies to a Peptide Encoded by Angiotensin II Complementary RNA", Apr. 1988, pp. 2518–2522.

Y. Shai et al., "Anti-Sense Peptide Recognition of Sense Peptides: Direct Quantitative Characterization with the Ribonuclease S–Peptide System Using Analytical High–Performance Affinity Chromatography" Biochem. 26, 669 (Feb. 10, 1987).

J. E. Blalock et al., "Hydropathic Anti–Complementarity of Amino Acids Based on the Genetic Code" Biochem. Biophys. Res. Comm. v. 121, 203-2-7 (May 31, 1984).

J. Kyte et al., "A Simple Method for Displaying the Hydropathic Character of a Protein" J. Mol. Biol. 157, 105-132 (1982).

G. Fassina et al., J. Cell Biochem., v. 35 No. 4, 362, 370, 371, (Dec. 1987).

*Primary Examiner*—Kevin J. Teska
*Attorney, Agent, or Firm*—Cushman, Darby & Cushman

[57] ABSTRACT

A computer-implemented method for designing at least one anti-peptide sequence having affinity for target peptide or a fragment thereof suitable for synthesizing peptides and micromolecules, assaying for a target peptides, purifying target peptides, and/or preventing proteolyis of a polypeptide includes identification of the members of the amino acid sequence of the target peptide and their anti-sense or hydropathically complementary amino acids and determining the moving average hydropathy for the target and anti-sense members. The resulting lowest hydropathy identifies the anti-sense amino acid sequence for the target peptide. The members of the target peptide amino acid sequence are obtained along with their member-specific hydropathic values with the hydropathic values summed as a moving average. Anti-sense or complementary amino acid members are identified from the moving average information to generate an array of anti-sense amino acid sequences. The hydropathic values of the array of anti-sense amino acids are obtained along with their moving average hydropathic values from which a hydropathic complementary score is obtained with the lowest score identifying the anti-sense amino acid sequence having affinity for the target peptide.

30 Claims, 5 Drawing Sheets

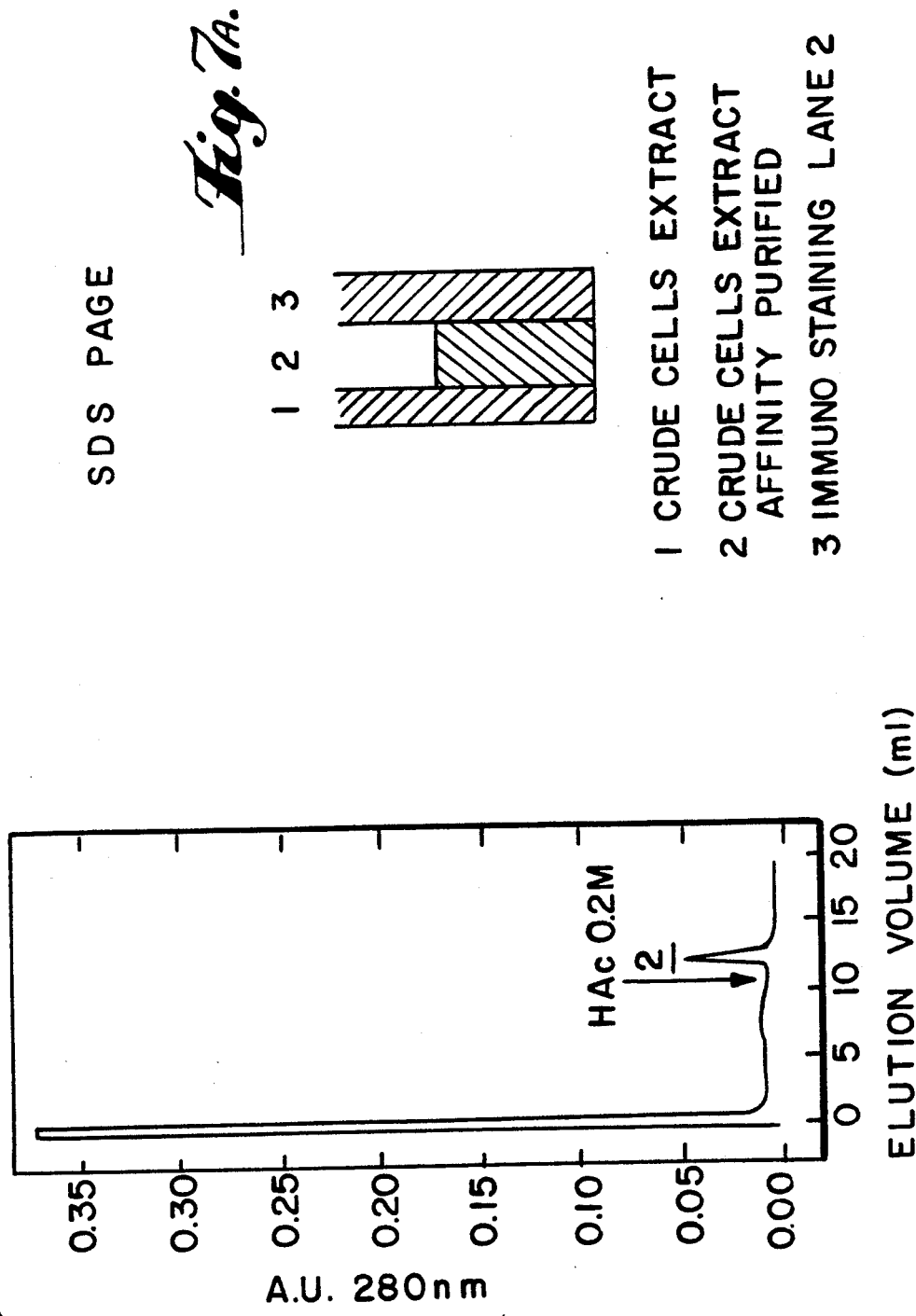

COMPUTER-ASSISTED DESIGN OF ANTI-PEPTIDES BASED ON THE AMINO ACID SEQUENCE OF A TARGET PEPTIDE

TECHNICAL FIELD

This invention relates to a computer operated method capable of generating target recognition amino acid sequences based solely on the amino acid sequence of a target peptide. The design amino acid sequences or anti-peptides may then be produced by chemical synthesis and utilized for recognizing and binding the target peptide. The anti-peptides may be designed so that they will evidence affinities and specificities which are high enough to permit the purification of the target peptide from even crude mixtures or biological extracts as well as the protection of the target peptide from proteolytic degradation, among other applications.

BACKGROUND ART

The ability of peptides generated from the noncoding strand of DNA to specifically recognize peptides coded by the complementary strand has been observed in several experimental systems (K. L. Bost et al, Proc. Natl. Acad. Sci. USA, 82, 1372 (1985); R. R. Brentani et al, Proc. Natl. Acad. Sci. (USA) 85, 364 (1988); T. S. Elton et al, Proc. Natl. Acad. Sci. USA, 85, 2518 (1988); Y. Shai et al, Biochem. 26, 669 (1987)).

Although the exact chemical nature of the interaction is still not well defined, it appears as if the recognition pattern of the sense and anti-sense peptides involves multi-site interactions between complementary amino acids along the sequence (Y. Shai et al, Biochem. 26, 669 (1987)). The recognition seems to occur independently of strict spatial conformation, but it may be dependent on the hydropathic profiles of the peptide (Y. Shai et al, Biochem. 26, 669 (1987); Y. Shai et al, "Protein Structure, Folding and Design 2", D. O. Oxender, ed., Alan R. Liss, New York, N.Y., (1987)).

The concept of sense:anti-sense interactions was derived from the observation that a unique pattern seemed to exist if the consequence of the transcription of complementary strands of DNA in the 5'-3' direction was considered (J. E. Blalock et al, Biochem. Biophys. Res. Comm. 121, 202 (1984).

It was noted that 1) the codons for hydrophilic amino acids on one strand are generally complemented by codons for hydrophobic amino acids on the other strand and vice versa.

2) The average tendency for "uncharged" (slightly hydrophilic) amino acids was to be complemented by codons for "uncharged" amino acids.

(J. E. Blalock et al, Biochem. Biophys. Res. C.mm., 121, 202 (1984).

The hydropathic values used to deduce these patterns were originally derived to predict protein domains in which each amino acid is assigned a numerical score ranging from +4.5 (very hydrophobic) to −4.5 (very hydrophilic) (J. Kyte et al, J. Mol. Biol. 157, 105 (1982).

The practical applications of sense anti-sense interactions have so far been limited to a few well defined systems for which DNA sequence information is available. The most frequent use has been in receptor purification where antibodies to anti-sense peptides were applied to purify the receptors for corLicotropin (ACTH), fibronectin and angrotensin II (K. L. Bost et al, Proc. Natl. Acad. Sci. (USA) 82, 1372 (1985); (R.R. Brentani et al, Proc. Natl. Acad. Sci. USA, 85, 364 (1988); T. S. Elton et al, Proc. Natl. Acad. Sci. USA, 85, 2518 (1988)). In addition, sense anti-sense interactions have been used to study other systems including the S-peptide, Arg$^8$-vasopressin, and neurophysin II (Y. Shai et al, Biochem 26, 669 (1987); G. Fassina et al, J. Cell Biochem , 35, 9 (1987)).

The generation of peptides with recognition properties towards the target peptide based on the ribonucleic acid (RNA) sequence coding for the target peptide was described by Bost, Smith and Blalock, supra. The sequences of these anti-sense peptides are deduced from the non-coding DNA strand which is complementary to the RNA segment encoding a target peptide. An essential requirement for the practice of this prior art method is the knowledge of the nucleic acid sequence encoding the target peptide. This method was later on successfully applied to other systems, thereby permitting the isolation of various target peptides or proteins. In some cases the method also aided in the identification of the receptor protein for the target peptide using antibodies raised against the anti-sense peptide (see, Brentani et al, supra; Elton et al, supra). However, the requirement that the DNA sequence encoding the target peptide be known is a significant drawback which prevents the more extensive use of this method.

Accordingly, there is still a need for a simpler and more efficient method of designing anti-peptides capable of displaying high affinity and specificity for a target peptide or fragments thereof which can be obtained in the absence of information on the ribonucleic acid (RNA) and/or deoxyribonucleic acid (DNA) sequences encoding the target peptide.

DISCLOSURE OF THE INVENTION

This invention relates to a computer operated method for designing at least one anti-peptide sequence having a high affinity of a target peptide or fragments for the target peptide. The amino acid sequence of the target peptide or a fragment thereof for which the high-affinity anti-peptide is desired is obtained and stored as members in a first array. A second array is obtained with hydropathic values of the corresponding members for the first array by obtaining member-specific hydropathic values from a data base of such values. The members of the second array are summed to provide moving average hydropathic values for each member of the second array with the moving average hydropathic values stored in a third array. Using the moving average hydropathic values of the third array and a data base of anti-sense or hydropathically complementary amino acids, a fourth array of anti-sense amino acids is stored from which selected anti-sense amino acid sequences are generated. The anti-sense amino acid sequences are stored in a fifth array and data from the hydropathic values of the corresponding members for the fifth array obtained for the member-specific hydropathic values from a data base of such values. A sixth array of hydropathic values of anti-sense amino acid sequences is created and a moving average of the anti-sense amino acids sequence of the fifth array is obtained and stored in a seventh array of moving average hydropathic values for the anti-sense amino acid sequences of the sixth array. For each anti-sense amino acid sequence in the seventh array, a hydropathic complementary score is generated with the lowest score identifying the antisense amino acid sequence of the fifth array having the affinity for the target array.

This invention also relates to a method of purifying a target polypeptide or fragments thereof, comprising:
(1) designing an anti-peptide sequence having high affinity and specificity for a target peptide or fragment thereof contained in the polypeptide by the computer operated method described above;
(2) synthesizing an anti-polypeptide comprising the anti-peptide sequence;
(3) contacting said anti-polypeptide with a sample comprising the target polypeptide to promote binding therebetween;
(4) separating said polypeptide-bound anti-polypeptide from the remaining components in the sample; and
(5) separating said polypeptide from the anti-polypeptide.

This invention also relates to a method of preventing the proteolysis of a polypeptide or fragments thereof in the presence of a proteolytic enzyme, which comprises
(1) designing an anti-peptide having high affinity and specificity for a target peptide or fragment thereof contained in the polypeptide by the computer operated method described above;
(2) synthesizing an anti-polypeptide comprising the anti-peptide sequence; and
(3) contacting said anti-polypeptide with a sample comprising the target polypeptide to promote binding therebetween, to thereby protect the polypeptide and prevent the proteolysis thereof when placed in contact with a proteolytic enzyme.

Also part of this invention is a method of preventing or reducing the binding of a first polypeptide or fragment thereof having affinity for a target peptide to a second polypeptide comprising said target peptide, said method comprising
(1) designing an anti-peptide sequence having affinity for the target peptide or a fragment thereof by the computer operated method described above;
(2) synthesizing an anti-polypeptide comprising said anti-peptide sequence;
(3) contacting said anti-polypeptide with a sample comprising said second polypeptide to provide binding therebetween to thereby prevent or reduce the binding of said second polypeptide to said first polypeptide in the presence thereof.

Still encompassed herein is a method of assaying for a target peptide or a fragment thereof, comprising
(1) designing an anti-peptide sequence having affinity for a target peptide or a fragment thereof contained in the polypeptide by the computer operated method described above;
(2) synthesizing an anti-polypeptide comprising the anti-peptide sequence;
(3) contacting said anti-polypeptide with a sample comprising the target polypeptide to promote binding therebetween.

Still encompassed herein is a method of assaying for a target peptide or a fragment thereof, comprising
(1) designing an anti-peptide sequence having affinity for a target peptide or a fragment thereof contained in the polypeptide by the computer operated method described above;
(2) synthesizing an anti-polypeptide comprising the anti-peptide sequence;
(3) contacting said anti-polypeptide with a sample comprising the target polypeptide to promote binding; and
(4) determining the presence of said polypeptide-bound antipolypeptide.

This invention also encompasses the formation of an anti-polypeptide macromolecule having affinity for a target peptide or a fragment thereof by a method comprising
(1) designing an anti-peptide sequence having affinity for a target peptide or a fragment thereof contained in the polypeptide by the computer operated method described above;
(2) synthesizing an anti-polypeptide comprising the anti-peptide sequence; and
(3) covalently binding at least two molecules of said anti-polypeptide to obtain said macromolecule.

A more complete appreciation of the invention and many of the attendant advantages thereof will be readily perceived as the same becomes better understood by reference to the following detailed description when considered in connection with the accompanying figures.

BRIEF DESCRIPTION OF DRAWINGS

FIG. 7 and FIG. 7A depict the results of a sodium dodecyl sulfate polyacrylamide gel electrophoresis (SDS-PAGE) of the raf oncogene product purified by affinity chromatography with the CG anti-peptide designed by the method of the invention corresponding to Example 5.

Figure 1:
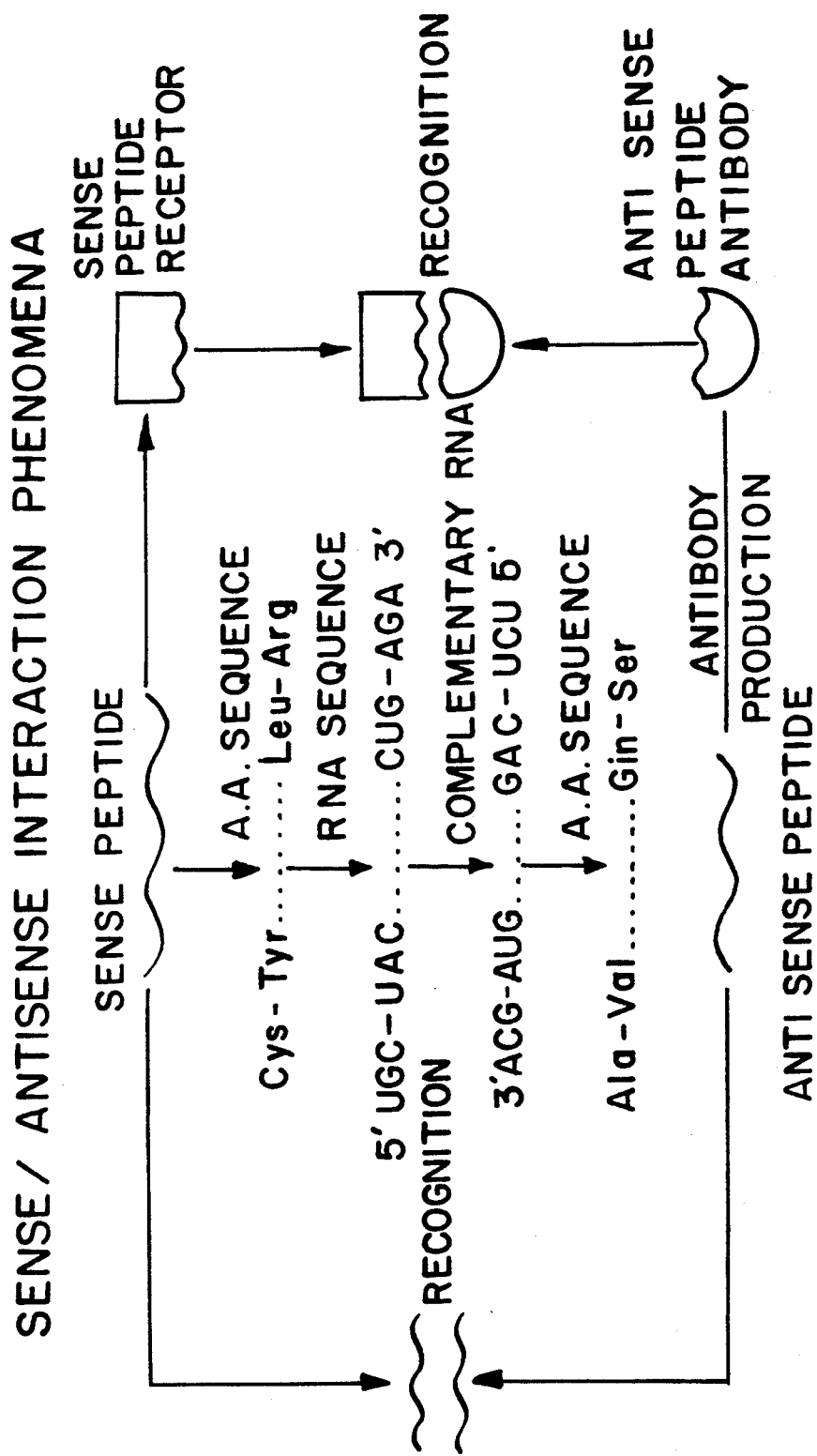
FIG. 1 is a schematic representation of sense:antisense peptide characteristics. Peptides produced by the non-coding strand of RNA (anti-sense strand) specifically recognize peptides produced from the coding strand (sense strand). Antibodies raised against the anti-sense peptide recognize receptor proteins for ,the sense peptide.
Figure 2:
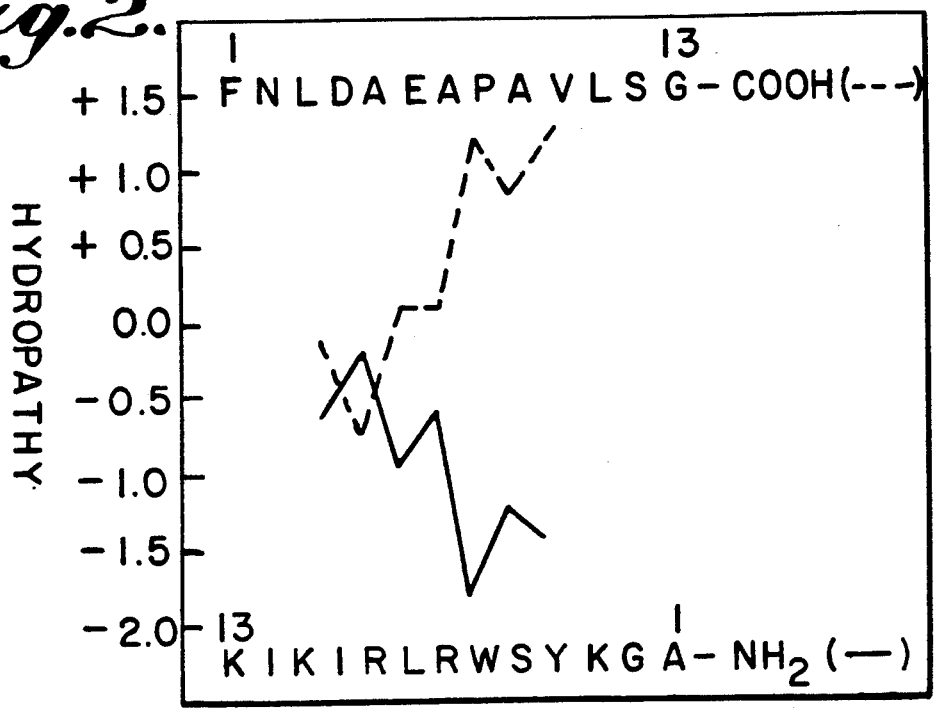
FIG. 2 provides a comparison between the hydropathy plots of a target 13mer peptide and a complementary peptide. The latter was obtained averaging the hydropathy values along 11 residues (R=11). The peptides are aligned antiparallel, and the hydropathy values are averaged on a window of 7 amino acids.
Figure 3:
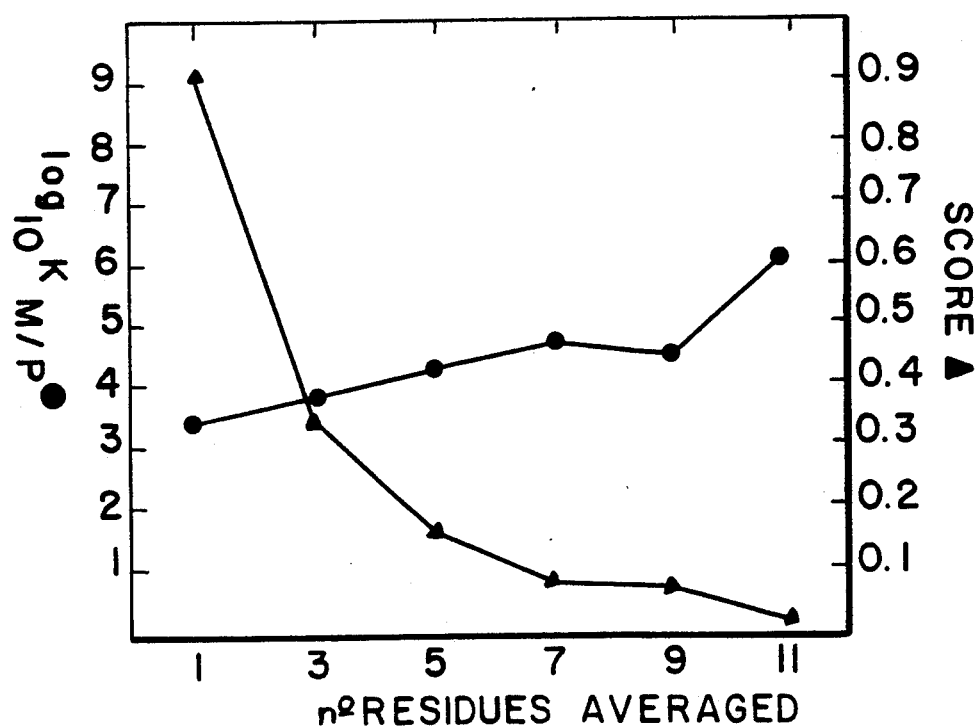
FIG. 3 shows the correlation between the binding affinities, the degree of averaging and the hydropathy scores obtained in Example 1. The hydropathy scores represent the degree of hydropathic complementarity which exists between the peptide and the anti-peptide. The values of the binding affinities $K_{M/P}$) were obtained by zonal elution on a column carrying the immobilized target peptide equilibrated at a flow rae of 1 ml/min with 100 mM $NH_4CH_3COO$ pH 5.7.
Figure 4:
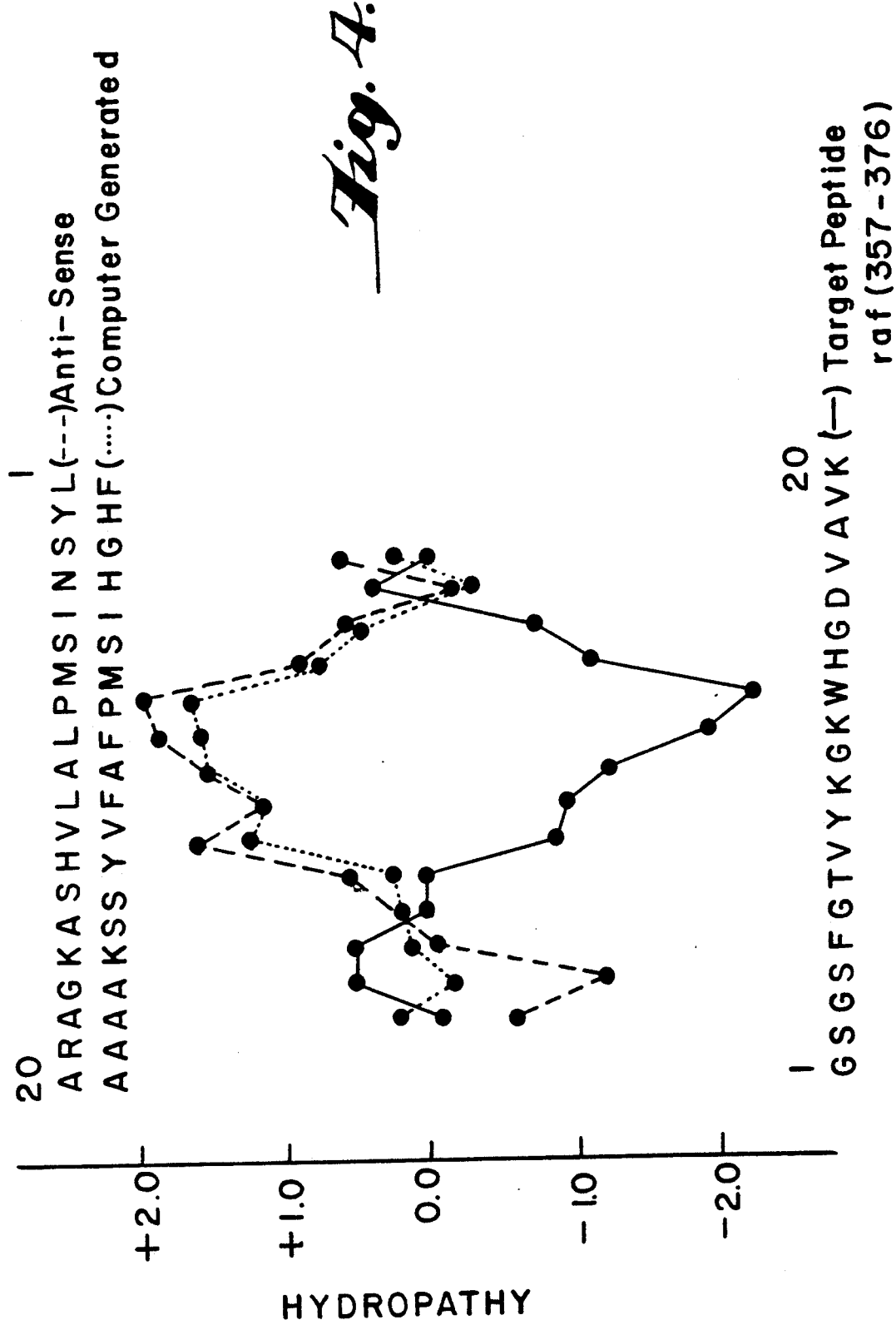
FIG. 4 shows a comparison between the hydropathy plots of the RNA-deduced anti-sense peptide (AS) and the computer-generated peptide in accordance with the invention (CG), and the target raf (356-375) peptide. Hydropathy values are averaged on a window of 7 amino acids.
Figure 5:
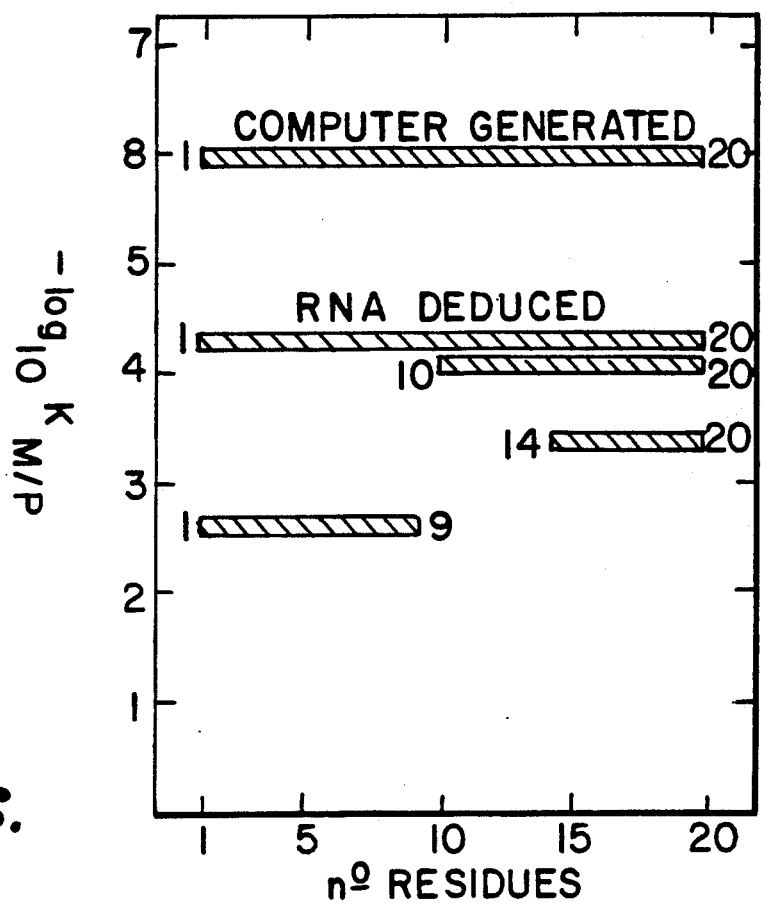
FIG. 5 shows a comparison between the binding affinities of the RNA-deduced anti-sense peptide (AS) and the computer-generated recognition peptide of the invention (CG) for the target raf (356-375) peptide. The values of the dissociation constants ($K_{M/P}$) are obtained in 0.1 M $NH_4CH_3COO$ pH 5.7.
Figure 6:
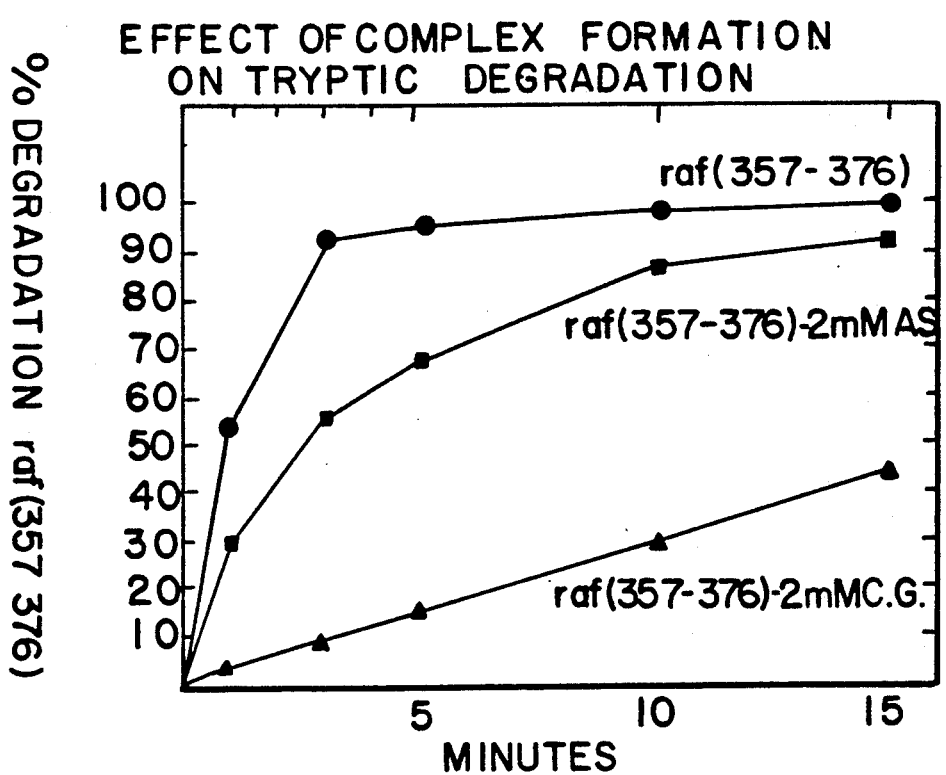
FIG. 6 depicts the effect of anti-peptide peptide complex formation on the rate of proteolysis of the target raf (356-375) peptide. The extent of degradation was monitored by reverse phase-high pressure liquid chromatography (RP-HPLC).

Other objects, advantages and features of the present invention will become apparent to those skilled in the art from the following discussion.

BEST MODE FOR CARRYING OUT THE INVENTION

This invention arose from the desire of the inventors to expand on known applications of peptide:peptide recognition properties. Accordingly, the present invention is based on the observation that complementary RNA codons code for hydropathically complementary amino acids in accordance with the amino acid hydropathy scoring system of Kyte and Doolittle (J. E. Blalock et al, Biophys Res Comm. 121, 202 (1984); J. Kyte et al, J. Mol. Biol. 157, 105 (1982)). The numerical values employed by the Kyte and Doolittle system are positive for hydrophobic amino acids and negative for hydrophilic amino acids In this system the hydropathy values range from +4.5, the largest for isoleucine (Ile), to −4.5, the smallest for arginine (Arg).

The Kyte and Doolittle hydropathy values are utilized in the present invention as part of a first database. These values are utilized in the present method to generate hydropathically complementary peptides based on the amino acid sequence of a target peptide or fragment thereof without knowledge of the RNA or DNA sequences encoding the target peptide. Accordingly, the present method neither requires nor utilizes nucleic acid sequence information to generate the complementary peptides or anti-peptides In accordance with the present method, anti-peptides can be designed which have higher binding constants for a target peptide than those anti-peptides obtained by a prior art method utilizing the complementary nucleic acid sequence to the RNA sequence encoding the target peptide.

Given the amino acid sequence of a target peptide composed of n residues $$P_1-P_2-P_3-\ldots-P_n,$$

each amino acid is assigned the corresponding hydropathy value $$h_1-h_2-h_3-\ldots-h_n$$

obtained from the Kyte and Doolittle scoring system (Kyte et al., J. Mol. Biol., 157: 105 (1982)). The Kyte and Doolittle hydropathy values are shown in Table 1 below.

TABLE 1

| Kyte and Doolittle Hydropathy Values | |
|---|---|
| Isoleucine | 4.5 |
| Valine | 4.2 |
| Leucine | 3.8 |
| Phenylalanine | 2.8 |
| Cysteine/cystine | 2.5 |
| Methionine | 1.8 |
| Alanine | 1.8 |
| Glycine | −0.4 |
| Threonine | −0.7 |
| Tryptophan | −0.9 |
| Serine | −0.8 |
| Tyrosine | −1.3 |
| Proline | −1.6 |
| Histidine | −3.2 |
| Glutamic acid | −3.5 |
| Glutamine | −3.5 |

TABLE 1-continued

| Kyte and Doolittle Hydropathy Values | |
|---|---|
| Aspartic acid | −3.5 |
| Asparagine | −3.5 |
| Lysine | −3.9 |
| Arginine | −4.5 |

Each amino acid is assigned a set of hydropathically complementary amino acids called "anti-sense" amino acids as follows.

$$Q_{1,a} - Q_{2,a} - Q_{3,a} - \cdots - Q_{n,a}$$
$$Q_{1,b} - Q_{2,b} - Q_{3,b} - \cdots - Q_{n,b}$$
$$Q_{1,c} - Q_{2,c} - Q_{3,c} - \cdots - Q_{n,c}$$
$$\vdots$$
$$Q_{1,m} - Q_{2,m} - Q_{3,m} - \cdots - Q_{n,m}$$

where the hydropathically complementary amino acids are shown in Table 2 below.

TABLE 2

| Sets of Hydropathically Complementary Amino Acids | |
|---|---|
| Ala—Arg, Cys, Gly, Ser | Leu—Gln, Glu, Lys |
| Arg—Ala, Pro, Ser, Thr | Lys—Leu, Phe |
| Asn—Ile, Val | Met—His |
| Asp—Ile, Val | Phe—Glu, Lys |
| Cys—Ala, Thr | Pro—Arg, Gly, Trp |
| Gln—Leu | Ser—Ala, Arg, Gly, Thr |
| Glu—Leu, Phe | Thr—Arg, Cys, Gly, Ser |
| Gly—Ala, Pro, Ser, Thr | Trp—Pro |
| His—Met, Val | Tyr—Ile, Val |
| Ile—Asn, Asp, Tyr | Val—Asp, Asp, His, Tyr |

The "moving average hydropathy" $a_i$ is then defined of the original sequence of a particular position as follows.

$$a_i = \left(\sum_{k=i-S}^{i+S} h_k(P_k)\right)/r,$$

wherein $S \leq i \leq n-S$,

S is defined as $(r-1)/2$, with r defined as the "run length" and being an odd number $\leq n$.

A "moving average hydropathy", $b_{j,i}$, can then be similarly defined for a particular candidate anti-peptide sequence, g, as follows $$b_{j,i} = \sum_k h'_{j,k}(Q_{j,k})/r,$$

wherein
K is $(i-S)$ to $k+S$),
$g_{j,1} = \Sigma Q_1,$
$g_{j,2} = \Sigma Q_2 \ldots$
$g_{j,n} = \Sigma Q_n.$ Amino acid sequences that minimize the hydropathic complementary score defined $\phi$, in accordance with the following equation $$\theta_j = \left(\sum_k (a_k + b_{j,k})^2/(n-2S)\right)^{\frac{1}{2}},$$

wherein k is (S+1) to (n−S), which are then defined as anti-peptide sequences.

Thus, the approach utilized in the present invention can be summarized as follows.

(1) Hydropathy values are assigned to each amino acid of the target peptide.

$$\begin{array}{cccccc} 1 & 2 & 3 & 4 & 5 & n \\ Phe(+2.8) & Asp(-3.5) & Leu(+3.8) & Asn(-3.5) & Ala(+3.8) & \ldots Gly(-0.4) \end{array}$$

(2) Each amino acid is assigned a corresponding set of anti-sense amino acids with their corresponding hydropathy values; and $$\begin{array}{cccccc} 1 & 2 & 3 & 4 & 5 & n \\ Gln(-3.5) & Ile(+4.5) & Glu(-3.5) & Ile(+4.5) & Arg(-4.5) & \ldots Ala(+1.8) \\ Lys(-3.9) & Val(+4.2) & Gln(-3.5) & Val(+4.2) & Gly(-0.4) & Pro(-1.6) \\ Glu(-3.5) & & Lys(-4.5) & & Ser(-0.8) & Ser(-0.8) \end{array}$$

(3) Hydropathy values are averaged along the sequence to create hydropathically complementary peptides.

For each "run length" r selected, a different set of peptides with different sequences and with different values of hydropathic complementarity score $\theta$ is attained.

Thus, this invention provides a computer-operated method for designing at least one anti-peptide sequence having a affinity, and optically specificity, for a target peptide or fragments thereof, comprising (1) obtaining the amino acid sequence $P_i$ of the target peptide or a fragment thereof $$P_i = P_1 - P_2 - P_3 - \ldots - P_n;$$

(2) entering into a computer said amino acid sequence as a first array;

(3) obtaining from a first data base a first hydropathic value for each member of the first array $$h_1 - h_2 - h_3 - \ldots - h_n;$$

(4) storing within the computer said first hydropathic values as a second array;

(5) summing the values in said second array to obtain a value $a_i$ for a first moving average hydropathy $a_i$ for each member of the first array in accordance with the formula $$a_i = \left( \sum_k h_k(P_k) \right)/r,$$

wherein
k is (i−S) to (i+S),
i is greater than S and up to or equal to (n−S),
S is (r−1)/2,
r is an odd numeral up to or equal to n, and
n is the number of amino acids in the sequence or fragment thereof;

(6) storing said values for the first moving average hydropathy in the computer as a third array;

(7) obtaining from a second anti-sense or hydropathically complementary amino acid data base a set comprising at least one anti-sense amino acid per member of the first array;

(8) storing within the computer said sets of at least one anti-sense amino acid as a fourth array;

(9) generating with the computer at least one anti-sense amino acid sequence by selecting one member $Q_{j,i}$ per set in the fourth array $$Q_{j,i} = Q_{j,1} - Q_{j,2} - Q_{j,3} - \ldots - Q_{j,n};$$

(10) storing within the computer said at least one anti-sense amino acid sequence as a fifth array;

(11) obtaining from the first data base a second hydropathic value $h'_{j,i}$ for each member of the fifth array $$h'_{j,i} - h'_{j,2} - h'_{j,3} - \ldots - h'_{j,n};$$

(12) storing within the computer said second hydropathic values as a sixth array;

(13) summing the values in said sixth array to obtain a value $b_{j,i}$ for a second moving average hydropathy for each member of the fifth array in accordance with the formula $$b_{j,i} = \left( \sum_k h'_{j,k}(Q_{j,k}) \right)/r,$$

wherein
K is in (i−S) to (i+S),
i is greater than S and up to or equal to (n−S),
j is 1 to the total number of sequences in the fifth array,
S is (r−1)/2,
r is an odd numeral up to or equal to n, and
n is the number of amino acids in the anti-peptide sequence or fragment thereof;

(14) storing said second average hydropathy values in the computer as a seventh array;

(15) generating within the computer one hydropathic complementary score $\theta_j$ for each anti-peptide sequence or fragment thereof in the fifth array in accordance with the formula $$\theta_j = \left( \left( \sum_k ((a_k + b_{j,k})^2)/(n - 2S) \right) \right)^{\frac{1}{2}},$$

wherein
K is (S+1) to (n−S), and
n and S are as defined above;

(16) storing within the computer the hydropathic complementary scores as an eighth array;

(17) identifying within the eighth array a group comprising at least the lowest score;

(18) identifying and selecting the at least one anti-sense sequence in the fifth array which corresponds to said at least one lowest score and identifying it as the at least one anti-peptide sequence having high affinity and selectivity for the target peptide or fragment thereof; and

(19) displaying said at least one anti-peptide sequence.

The method of this invention may further comprise

(20) assigning said at least one anti-peptide sequence selected in step (18) an affinity value; wherein the highest affinity value is assigned the an ti-peptide having the lowest hydropathic complementary score and the lowest affinity value is assigned the anti-peptide having the highest score of the group.

In a preferred embodiment of the method of the invention, the amino acid sequence of the target peptide is entered into the computer in step (2) by means of a keyboard However, other means may also be utilized. For example, the data may be input into the computer from another computer, may be provided as the output from another computer program or from an amino acid sequencing apparatus, and the like.

In another preferred embodiment of the invention the group of lowest hydropathic complementary scores identified in step (17) may comprise anywhere from 1 to 1,000 scores, and even more. The number of anti-peptides identified and selected in step (18) also corresponds to the number of scores identified above. If a lower number of scores is desired in order to simplify the selection process, a preferred number of scores identified in step (17) may comprise about 5 to 500 scores, and still more preferred the number of scores may be about 10 to 100. However, groups comprising different numbers of scores may also be utilized as needed.

In still another preferred embodiment of this invention the at least one anti-peptide sequence selected in step (18) may be output by printing.

In yet another preferred embodiment the anti-polypeptide sequence comprises all D amino acids which are resistant to proteolysis and therefore longer lasting for most applications Another preferred embodiment comprises all L-amino acids.

In a particularly preferred embodiment of this invention the method utilizes weighted averages. By means of example, the moving average hydropathy scores $$a_i = \left(\sum_k h_k\right)/r,$$

and $$b_{j,i} = (\Sigma h'_{j,k})/r,$$

are replaced with weighted average hydropathy scores, e.g., $$a_i = \sum_{k=1}^{n} h_k w_{i,k},$$

and $$b_{j,i} = \sum_{k=1}^{n} h'_{j,k} w_{i,k},$$

where the $w_{i,k}$ values are chosen such that $$\sum_{k}^{n} w_{i,k} = 1$$

for all values of i between and including 1 and n. Various methods of weight averaging are known in the art and need not be described herein. Any and all may be used herein.

Also part of the invention is a method of purifying a target polypeptide or a fragment thereof, comprising
(1) designing an anti-peptide sequence having affinity for a target peptide or a fragment thereof contained in the polypeptide by the computer operated method described above;
(2) synthesizing an anti-polypeptide comprising the anti-peptide sequence;
(3) contacting said anti-polypeptide with a sample comprising the target polypeptide to promote binding therebetween;
(4) separating said polypeptide-bound anti-polypeptide from the remaining components in the sample; and
(5) separating said polypeptide from the anti-polypeptide.

In a particularly preferred embodiment of the above method step (3) is conducted in two parts. In the first part the anti-peptide is immobilized on a solid support such as a chromatographic column, resin, or other solid support, and the second part is conducted by contacting the anti-peptide bound to the solid support with a sample comprising the polypeptide to promote high affinity, and optionally specificity, binding between the polypeptide and the anti-polypeptide.

In a preferred embodiment, the anti-polypeptide consists essentially of the anti-peptide.

In yet another preferred embodiment the anti-polypeptide sequence comprises all D amino acids which are resistant to proteolysis and therefore longer lasting for most applications. Another preferred embodiment comprises all L-amino acids.

In another preferred embodiment of the invention, the method described above is conducted in a manner such that the anti-peptide of step (2) consists essentially of the sequences of the anti-peptide.

Also provided herein is a method of preventing the proteolysis of a polypeptide in the presence of a proteolytic enzyme, which comprises
(1) designing an anti-peptide having high affinity and specificity for a target peptide or fragment thereof contained in the polypeptide by the computer operated method described above;
(2) synthesizing an anti-polypeptide comprising the anti-peptide sequence; and
(3) contacting said anti-polypeptide with a sample comprising the target polypeptide to promote binding therebetween, to thereby protect the polypeptide and prevent the proteolysis thereof when placed in contact with a proteolytic enzyme.

In a preferred embodiment, the anti-polypeptide consists essentially of the anti-peptide.

In yet another preferred embodiment the anti-polypeptide sequence comprises all D amino acids which are resistant to proteolysis and therefore longer lasting for most applications. Another preferred embodiment comprises all L-amino acids.

Based on the method developed by the inventors, it is possible to derive recognition peptides or anti-peptides which have substantially high binding affinities to a target amino acid sequence given only the amino acid sequence of the target peptide. This can be done in the absence of any information relating to the RNA and/or DNA sequences encoding the target peptide. More importantly, it is also possible by optimizing the hydropathic complementary score obtained for each sequence of anti-peptides to choose sequences that have higher affinities for the target peptide than the anti-peptides derived by the DNA-based method. The present method enables the application of sense:anti-sense interactive concepts to the practical purpose of designing by a computer-operated method highly specific anti-peptides which bind to a target peptide or fragments thereof with high affinities.

In general, it can be said that by practicing the method of the invention, anti-peptides having affinities for the target peptide substantially higher than those obtained by the DNA-based method are obtained. In many cases the affinity constants for the anti-peptides obtained by the method of the invention can be higher by a factor of greater than about 10 than those obtained by the DNA-based method of the prior art. Typically, the affinity constants obtained in accordance with the method of the invention are higher than the constants obtained by the DNA-based method by at least an about 50-fold factor.

In many instances an increase in the run length r is characterized by a decrease in the hydropathic complementary score $\theta$ and is accompanied by the same time by an increase in the binding affinities of the anti-peptides for the target peptide. Accordingly, the present method permits the designing of anti-peptides with binding properties for a target peptide or fragment thereof while at the same time permitting the modulation of the binding affinities by varying the degree of hydropathic complementarity of the target peptide and the anti-peptide.

Also provided herein is a method of preventing or reducing the binding of a first polypeptide or fragments thereof having affinity for a target peptide, to a second polypeptide comprising said target peptide, the method comprising (1) designing an anti-peptide sequence having affinity for the target peptide or a fragment thereof by the computer operated method described above;

(2) synthesizing an anti-polypeptide comprising said anti-peptide sequence;

(3) contacting said anti-polypeptide with a sample comprising said second polypeptide to provide binding therebetween to thereby prevent or reduce the binding of said second polypeptide to said first polypeptide in the presence thereof.

In a preferred embodiment, the anti-polypeptide consists essentially of the anti-peptide.

In yet another preferred embodiment the anti-polypeptide sequence comprises all D amino acids which are more resistant to proteolysis and therefore longer lasting for most applications. Another preferred embodiment comprises all L-amino acids.

Also provided herein is a method of assaying for a target peptide or a fragment thereof, comprising (1) designing an anti-peptide sequence having affinity for a target peptide or a fragment thereof contained in the polypeptide by the computer operated method described above;

(2) synthesizing an anti-polypeptide comprising the anti-peptide sequence and (3) contacting said anti-polypeptide with a sample comprising the target polypeptide to promote binding therebetween; and (4) determining the presence of said polypeptide-bound anti-polypeptide.

In a preferred embodiment, the anti-polypeptide consists essentially of the anti-peptide.

In yet another preferred embodiment the anti-polypeptide sequence comprises all D amino acids which are resistant to proteolysis and therefore longer lasting for most applications. Another preferred embodiment comprises all L-amino acids.

In still another preferred embodiment of the above method the anti-polypeptide is labeled Typically, the anti-polypeptide may be labeled by means of an enzyme, radioactive atom and other means known in the art. Preferred is an anti-polypeptide which is radiolabeled.

In another preferred embodiment of the above method the anti-polypeptide is bound to a said carrier. Types of solid carriers and methods for binding the anti-polypeptide to the carrier are known in the art and need not be further described herein.

In still a more preferred embodiment of the above method step (4) is conducted by (a) designing an anti-(anti-polypeptide) sequence having affinity for said anti-polypeptide or a fragment thereof by the above computer operated method;

(b) synthesizing a second anti-anti-polypeptide comprising said first anti-(anti-polypeptide) sequence;

(c) labeling said second anti-anti-polypeptide;

(d) contacting said labeled anti-anti-polypeptide with said sample comprising said polypeptide-bound anti-polypeptide to promote binding therebetween;

(e) separating said (polypeptide-anti-polypeptide)-bound labeled anti-anti-polypeptide; and (f) determining the presence or amount of label present.

The technology enabling the above steps for the assay method are known in the art and need not be described here in detail. An artisan would know how and where to obtain such information.

Having now generally described this invention, the same will be better understood by reference to certain specific examples, which are included herein for purposes of illustration only and are not intended to be limiting of the invention or any embodiment thereof, unless so specified.

EXAMPLES

Example 1: Design of Anti-sense Recognition Peptides with the Method of the Invention: A-Obtaining Target Peptide Sequence A membrane glycoprotein implicated in liver tumorigenic processes was chosen as a target peptide (Raunio, H., et al., Exp. Cell Res 173:596 (1987)). This protein was purified by two-dimensional PAGE and a portion of the amino terminus (13 amino acids) was deduced by gas-phase amino acid sequencing techniques. (Parmalee, D., et al., "Techniques in Protein Chemistry, A. C. Hugli, ed., Academic Press. San Diego, Calif, In Press). The goal was to design a recognition peptide to the amino terminus which could be used to affinity purify larger amounts of this protein.

Since DNA sequence information was not available for this unknown protein, there were more than 1,700,000 sequences that could correspond to the DNA derived anti-sense sequence of the 13 amino acid section.

Two design systems based on the anti-sense theory were developed in an attempt to obtain recognition peptides to the amino terminus of the glycoprotein. The first system is based on codon frequency patterns. The second system involves the use of hydropathic score (MAHS) originally derived for the hydropathic scoring system of Kyte and Doolittle (J. Kyte et al, J. Mol. Biol., 157:105 (1982)).

Example 2: Design of Anti-sense Recognition Peptides with the Method of the Invention: B- Recognition Peptides Based on Codon Frequency Patterns In this system, two peptide sequences (Codon 1 and 2) were derived on the basis of codon frequency usage patterns (S. Aota, et al, Nucl Acid Res , 16 Supple 315 (1988); D. Hatfield et al, Biochem. Int 13, 835 (1986)).

The first peptide (Codon 1) was derived on the basis of codon usage as they were tabulated from the GenBank genetic sequence data (Aota, S., et al., Nucl. Acid Res 16 Suppl 315 (1988)). The codon usage data for the rat was taken for the determination since the glycoprotein of interest was isolated from a rat liver (H. Raunio et al, Exp. Cell Res., 173:596 (1987)). The codons corresponding to the amino acids (F,N,L,D,A,E,P,V,S,G) in the 13-mer section of the amino terminal were examined and the most frequently used codons for a particular amino acid were chosen for the determination of the "best guess" anti-sense peptide sequence as shown in Table 2 below.

TABLE 1-continued

List of amino acids, hydropathic values and corresponding anti-sense amino acid partners.

| AMINO ACID | HYDROPATHIC VALUE | ANTI-SENSE AMINO ACID |
|---|---|---|
| Leu (L) | 3.8 | Q,E,K |
| Lys (K) | −3.9 | L,F |
| Met (M) | 1.9 | H |
| Phe (F) | 2.7 | E,K |
| Pro (P) | −1.6 | R,G,W |
| Ser (S) | −0.8 | A,R,G,T |
| Thr (T) | −0.7 | A,C,G,S |
| Trp (W) | −0.9 | P |
| Tyr (Y) | −1.3 | I,V |

TABLE 2

Design of Anti-Sense Recognition Peptides with the Method of the Invention: C. Recognition Peptides by Computer Assisted Design

| TARGET AA AA SEQUENCE | NH$_2$—Phe Asn Leu Asp Ala Glu Ala Pro Ala Val Leu Ser Gly—COOH |
|---|---|
| BEST GUESS RNA SEQUENCE | 5'-UUC AAC CUG GAC GCC GAG GCC CCC GCC GUG CUG AGC GGC-3' |
| AA SEQUENCE COMPLEMENTARY RNA SEQUENCE | 5'-GCC GCU CAG CAC GGC GGG GGC CUC GGC GUC CAG GUU GAA-3' |
| RECOGNITION AA SEQUENCE CODON-1 | NH$_2$—Ala ala gln His Gly Gly Gly Leu Gly Val Gln Val Glu—COOH |

As second peptide (Codon 2) was determined similarly on the basis of the relative tRNA levels for the codons as they occur in rabbit liver (D. Hatfield et al, Biochem. Int. 13, 835 (1986); D. Hatfield et al, Biochim. Biophys. Acta 564, 414 (1979)). This pattern was examined because overall codon choice patterns appear to be roughly common between mammalian species, though there might be some interorgan variations. (Note: Relative tRNA ratios for a particular amino acid differ between the liver and reticulocytes in rabbits.) The sequence derived from the second recognition peptide was AAQHGRGPGIQIE (Codon-2).

Example 3: Design of Anti-Sense Recognition Peptides with the Method of the Invention: C. Recognition Peptides by Computer Assisted Design Since the original sense:anti-sense theory was hypothesized on the basis of hydropathically complementary values (Blalock, J. E. et al, Biochem Biophys. Res. Comm., 121, 202 (1984)) for the second system a computer program was developed to seek out those sequences which maximize hydropathic complementary. The program takes each amino acid of the target peptide and notes both its hydropathic score and the set of amino acids that are its theoretically possible anti-sense partners. This information is bonded in Table 1 below.

TABLE 1

List of amino acids, hydropathic values and corresponding anti-sense amino acid partners.

| AMINO ACID | HYDROPATHIC VALUE | ANTI-SENSE AMINO ACID |
|---|---|---|
| Ala (A) | 1.8 | R,C,G,S |
| Arg (R) | −4.5 | A,P,S,T |
| Asn (N) | −3.5 | I,V |
| Asp (D) | −3.5 | I,V |
| Cys (C) | 2.5 | A,T |
| Gln (Q) | −3.5 | L |
| Flu (E) | −3.5 | L,F |
| Gly (G) | −0.4 | A,P,S,T |
| His (H) | −3.2 | M,T |
| Ile (I) | 4.5 | N,D,Y |
| Val (V) | 4.2 | N,D,H,Y |

The program then defines a "moving average hydropathic score" for the target sequence at each position (Kyte, J., et al, J. Mol Biol. 157:105 (1982)). Likewise, it defines a "moving average hydropathic score" for a particular partner. Those partner sequences that minimize the root means square of the scores at each position are chosen as possible recognition sequences For each run length "r" (this corresponds to the number of amino acids over which the score is averaged) a different sequence(s) is obtained and a complementarity score is found (low scores win). The sequences and scores obtain for the target 13-mer (AVG 1,3,5,7,9,11) are shown in Table 3 below.

TABLE 3

Sequence and scores for the 13-mer Polypeptide TARGET PEPTIDE F N L D A E A P A V L S G (GP-1)

| # POSITIONS AVERAGED | COMPLEMENTARITY SCORE | SEQUENCE | NAME |
|---|---|---|---|
| 1 | 0.906 | TAKDSGSLSVKVE | AVG-1 |
| 3 | 0.336 | AGKDSGGFSVKVE | AVG-3 |
| 5 | 0.152 | PAKDSGSFSVKVK | AVG-5 |
| 7 | 0.075 | TAKDSWSFSVKVK | AVG-7 |
| 9 | 0.066 | AAKDSRGLGIEIE | AVG-9 |
| 11 | 0.016 | AGKYSWRLRIKIK | AVG-11 |

In some cases more than one sequence is possible the scores are identical

Example 4: Evaluation of Recognition Peptides by HPLAC

The recognition of the target peptide by the anti-sense peptides was evaluated by high performance affinity chroma tography (I. Chaiken, Ed., "Analytical Affinity Chromatography," CRC Press, Boca Raton, 1987). This system was chosen because it allows direct measurement of molecular interactions and it is not limited by either molecular size or by the need for a specialized detection system. The target 13-mer (GP-1) was immobilized on an affinity support system. The binding properties to the target peptide were evaluated by zonal elution methods (FIG. III) (Y. Shai et al, Biochem., 26:669 (1987)). The anti-sense recognition peptides were eluted on the sense column and the retardation volume of the peptide (V) was compared to the column void volume (Vo). Equilibrium binding constants were determined by loading varying amounts of the anti-sense peptides on the column and employing the equation:

$$\frac{1}{v-v_0} = \frac{K_{M/P}}{M_T} + \frac{[P]}{M_T}$$

where
$K_{M/P}$ represents the dissociation constant for the binding process,
$M_T$ is the amount of target peptide immobilized and
[P] represents the amount of recognition peptide eluted E. Swaisgood et al, Biochem., 25:4148 (1986)).

The $K_{M/P}$ values are obtained subsequent to extrapolation to [P]=0.

The $K_{M/P}$ values for the recognition peptide were determined using this system. The data obtained for the binding constants are shown in Table 4 below.

TABLE 4

Equilibrium binding constants ($K_{M/P}$ for anti-sense recognition peptides.

| PEPTIDE | SEQUENCE | $K_{M/P}$ (μM) |
|---|---|---|
| CODON-1 | AAQHGGGLGVQVE | 920 |
| CODON-2 | AAQHGRGFGIQIE | 460 |
| AVG-1 | TAKDSGSLSVKVE | 460 |
| AVG-3 | AGKDSGGFSVKVE | 160 |
| AVG-5 | PAKDSGSFSVKVK | 59 |
| AVG-7 | TAKDSWSFSVKVK | 22 |
| AVG-9 | AAKDSRGLGIEIE | 40 |
| AVG-11 | AGKYSWRLRIKIK | 0.7 |

Values were obtained by zonal elution on a column with immobilized target peptide (GP-1) equilibrated with 100 mM NH₄OAc, pH = 5.7 with column flow rate of 1.0 ml/min.

Both Codon 1 and Codon 2 gave binding constants in the millimolar range. In contrast, the computer generated recognition peptides gave equilibrium constants ranging from $1 \times 10^{-4}$ to $2 \times 10^{-7}$ M. Within this range, an interesting pattern seems to exist between affinity and the hydropathic complementary score.

It seems that when the score is lowered the degree of recognition increases, and that in this particular system the recognition can be enhanced between three and four orders of magnitude relative to the codon frequency pattern.

Example 5: Comparison of Affinity Characteristics of Anti-peptides Obtained by the Inventive Method with those for a DNA-Derived Anti-sense Peptide In order to evaluate the general applicability of the complementary scoring program, a comparison was made between the DNA derived anti-sense peptide and a computer generated recognition-peptide. The model target peptide chain was the putative ATP binding region of the raf (Ishikawa, F., et al., Mol. Cell Biol. 7:1226 (1987)). This region is 20 amino acid-residues long (raf 357-376) and the DNA sequence information is published (F. Ishikawa, et al Mol. Cell Biol. 7, 1226 (1987)). To compare the relative affinities of the DNA derived anti-sense peptide (FAR-LYSNISMPLALV-HSAKGARA) and the computer generated recognition peptide (FARCG-FHGHISMDFAFVYSSKAAAA), the raf ATP binding region (GSGSFGTVYKGKWHGDVAVK) was immobilized on an affinity support and the two anti-sense peptides evaluated by HPLAC techniques. The affinity characteristics of two DNA-derived anti-peptides are shown in Table 5 below.

TABLE 5

Equilibrium Binding Constants ($K_{M/P}$) for DNA Derived (FAR) and Computer Generated (FAR = -CG) Anti-sense Recognition Peptides to the Putative ATP Binding Site of the raf Oncogene.

| PEPTIDE | SEQUENCE | $K_{M/P}$ (μM) |
|---|---|---|
| FAR | LYSNISMPLALVHSAKGARA | 377 |
| FAR-CG | FHGHISMPFAFVYSSKAAAA | 8 |

In this system, the computer generated peptide demonstrates an almost 50-fold higher affinity for the target peptide when compared to the DNA derived anti-sense peptide.

The invention now being fully described, it will be apparent to one of ordinary skill in the art that many changes and modifications can be made thereto without departing from the spirit or scope of the invention as set forth herein.

We claim:

1. A method of purifying a target polypeptide or a fragment thereof, comprising
   (1) designing an anti-peptide sequence having high affinity and specificity for a target peptide or a fragment thereof contained in said polypeptide by
   (I) obtaining an amino acid sequence $P_i$ of the target peptide or a fragment thereof $$P_i = P_1 - P_2 - P_3 - \ldots - P_h;$$

(II) entering into a computer said amino acid sequence as a first array;
   (III) obtaining from a first data base a first hydropathic value for each member of the first array $$h_1 - h_2 - h_3 - \ldots - h_n;$$

(IV) storing within the computer said first hydropathic values as a second array;
   (V) summing the values in said second array to obtain a value $a_i$ for a first moving average hydropathy $a_i$ for each member of the first array in accordance with $$a_i = \left( \sum_k h_k(P_k) \right) / r$$

wherein
   k is (i−S) to (i+S),
   i is greater than S and up to or equal to (n−S),
   S is (r−1)/2,
   r is an odd numeral up to or equal to n, and
   n is the number of amino acids in the sequence or fragment thereof;
   (VI) storing said values for the first moving average hydropathy in the computer as a third array;
   (VII) obtaining from a second anti-sense or hydropathically complementary amino acid data base a set comprising at least one anti-sense amino acid per member of the first array;

(VIII) storing within the computer said sets of at least one anti-sense amino acid as a fourth array;

(IX) generating with the computer at least one anti-sense amino acid sequence by selecting one member $Q_{j,i}$ per set in the fourth array $$Q_{j,i} = Q_{j,1} - Q_{j,2} - Q_{j,3} - \ldots - Q_{j,n'};$$

(X) storing within the computer said at least one anti-sense amino acid sequence as a fifth array;

(XI) obtaining from the first data base a second hydropathic value $h_{j,i}$ for each member of the fifth array $$h'_{j,i} - h'_{j,2} - h'_{j,3} - \ldots - h'_{j,n'};$$

(XII) storing within the computer said second hydropathic values as a sixth array;

(XIII) summing the values in said sixth array to obtain a value $b_{j,i}$ for a second moving average hydropathy for each member of the fifth array in accordance with $$b_{j,i} = \left( \sum_{k} h'_{j,k}(O_{j,k}) \right) / r$$

wherein
K is $(i-S)$ to $(i+S)$,
i is greater than S and up to or equal to $(n-S)$,
j is 1 to the total number of sequences in the fifth array,
S is $(r-1)/2$,
r is an odd numeral up to or equal to n, and peptide sequence or fragment thereof;

(XIV) storing said second average hydropathy values in the computer as a seventh array;

(XV) generating within the computer one hydropathic complementary score $\theta_j$ for each anti-peptide sequence or fragment thereof in the fifth array in accordance with $$\theta_j = ((\Sigma (a_k + b_{j,k})^2)/(n-2S))^{1/2},$$

wherein
K is $(S+1)$ to $(n-S)$, and
n and S are as defined above;

(XVI) storing within the computer the hydropathic complementary scores as an eighth array;

(XVII) identifying within the eighth array a group having a lowest score;

(XVIII) identifying and selecting the at least one anti-sense sequence in the fifth array which corresponds to said at least one lowest score and identifying it as the at least one anti-peptide sequence having high affinity and selectivity for the target peptide or fragment thereof (2) synthesizing an anti-[poly]peptide comprising the anti-peptide sequence;

(3) contacting said synthesized anti-peptide with a sample comprising the target polypeptide to promote binding therebetween;

(4) separating said polypeptide-bound anti-peptide from the remaining components in the sample; and (5) separating said peptide from the anti-peptide.

2. The method of claim 1, wherein step (3) comprises (3a) immobilizing said anti-peptide on a solid support;

(3b) contacting said anti-peptide bound to the solid support with a sample comprising the target polypeptide to promote high affinity and specificity binding between the peptide and said anti-peptide.

3. The method of claim 1, wherein the anti-polypeptide of step (2) consists essentially of said anti-peptide.

4. The method of claim 1, wherein said at least one anti-peptide comprises L-amino acids.

5. The method of claim 1, wherein said at least one anti-peptide comprises D-amino acids.

6. A method of preventing proteolysis of a polypeptide in the presence of a proteolytic enzyme, comprising (1) designing an anti-peptide having high affinity and specificity for a target peptide or fragment thereof contained in the polypeptide by (I) obtaining an amino acid sequence $P_i$ of the target peptide or a fragment thereof $$P_i = P_1 - P_2 - P_3 - \ldots - P_h;$$

(II) entering into a computer said amino acid sequence as a first array;

(III) obtaining from a first data base a first hydropathic value for each member of the first array $$h_1 - h_2 - h_3 - \ldots - h_n;$$

(IV) storing within the computer said first hydropathic values as a second array;

(V) summing the values in said second array to obtain a value $a_i$ for a first moving average hydropathy $a_i$ for each member of the first array in accordance with $$a_i = \left( \sum_{k} h_k(P_k) \right) / r$$

wherein
k is $(i-S)$ to $(i+S)$,
i is greater than S and up to or equal to $(n-S)$, S is $(r-1)/2$, r is an odd numeral up to or equal to n, and
n is the number of amino acids in the sequence or fragment thereof;

(VI) storing said values for the first moving average hydropathy in the computer as a third array;

(VII) obtaining from a second anti-sense or hydropathically complementary amino acid data base a set comprising at least one anti-sense amino acid per member of the first array;

(VIII) storing within the computer said sets of at least one anti-sense amino acid as a fourth array;

(IX) generating with the computer at least one anti-sense amino acid sequence by selecting one member $Q_{j,i}$ per set in the fourth array $$Q_{j,i} = Q_{j,1} - Q_{j,2} - Q_{j,3} - \ldots - Q_{j,n'};$$

(X) storing within the computer said at least one anti-sense amino acid sequence as a fifth array;

(XI) obtaining from the first data base a second hydropathic value $h_{j,i}$ for each member of the fifth array $h'_{j,i}-h'_{j,2}-h'_{j,3}-\ldots-h'_{j,n}$';

(XII) storing within the computer said second hydropathic values as a sixth array;

(XIII) summing the values in said sixth array to obtain a value $b_{j,i}$ for a second moving average hydropathy for each member of the fifth array in accordance with $$b_{j,i} = \left( \sum_k h'_{j,k}(O_{j,k}) \right)/r$$

wherein
K is (i−S) to (i+S),
i is greater than S and up to or equal to (n−S),
j is 1 to the total number of sequences in the fifth array,
S is (r−1)/2,
r is an odd numeral up to or equal to n, and
n is the number of amino acids in the anti-peptide sequence or fragment thereof;

(XIV) storing said second average hydropathy values in the computer as a seventh array;

(XV) generating within the computer one hydropathic complementary score $\theta_j$ for each anti-peptide sequence or fragment thereof in the fifth array in accordance with $$\theta_j = ((\Sigma (a_k + b_{j,k})^2)/(n - 2S))^{\frac{1}{2}},$$

wherein
K is (S+1) to (n−S), and
n and S are as defined above;

(XVI) storing within the computer the hydropathic complementary scores as an eighth array a group having a lowest score;

(XVII) identifying within the eighth array a group having a lowest score;

(XVIII) identifying and selecting the at least one anti-sense sequence in the fifth array which corresponds to said at least one lowest score and identifying it as the at least one anti-peptide sequence having high affinity and selectivity for the target peptide or fragment thereof (2) synthesizing an anti-polypeptide comprising the anti-peptide sequence; and (3) contacting said anti-polypeptide with a sample comprising the target polypeptide to promote binding therebetween, to thereby protect the polypeptide and prevent the proteolysis thereof when placed in contact with a proteolytic enzyme.

7. The method of claim 6, wherein
said at least one anti-peptide comprises L-amino acids.

8. The method of claim 6, wherein
said at least one anti-peptide comprises D-amino acids.

9. The method of claim 6, wherein
the anti-polypeptide of step (2) consists essentially of the anti-peptide.

10. A method of preventing or reducing the binding of a first polypeptide or fragments thereof having affinity for a target peptide to a second polypeptide comprising said target peptide, comprising 1) designing an anti-peptide sequence having affinity for the target peptide or a fragment thereof by (I) obtaining an amino acid sequence $P_i$ of the target peptide or a fragment thereof $P_i = P_1 - P_2 - P_3 - \ldots - P_h$;

(II) entering into a computer said amino acid sequence as a first array;

(III) obtaining from a first data base a first hydropathic value for each member of the first array $h_1 - h_2 - h_3 - \ldots - h_n$;

(IV) storing within the computer said first hydropathic values as a second array;

(V) summing the values in said second array to obtain a value $a_i$ for a first moving average hydropathy $a_i$ for each member of the first array in accordance with $$a_i = \left( \sum_k h_k(P_k) \right)/r$$

wherein
k is (i−S) to (i+S),
i is greater than S and up to or equal to (n−S),
S is (r−1)/2,
r is an odd numeral up to or equal to n, and
n is the number of amino acids in the sequence or fragment thereof;

(VI) storing said values for the first moving average hydropathy in the computer as a third array;

(VII) obtaining from a second anti-sense or hydropathically complementary amino acid data base a set comprising at least one anti-sense amino acid per member of the first array;

(VIII) storing within the computer said sets of at least one anti-sense amino acid as a fourth array;

(IX) generating with the computer at least one anti-sense amino acid sequence by selecting one member $Q_{j,i}$ per set in the fourth array $Q_{j,i} = Q_{j,1} - Q_{j,2} - Q_{j,e} - \ldots - Q_{j,n}$;

(X) storing within the computer said at least one anti-sense amino acid sequence as a fifth array;

(XI) obtaining from the first data base a second hydropathic value $h_{j,i}$ for each member of the fifth array $h'_{j,i} - h'_{j,2} - h'_{j,3} - \ldots - h'_{j,n}$';

(XII) storing within the computer said second hydropathic values as a sixth array;

(XIII) summing the values in said sixth array to obtain a value $b_{j,i}$ for a second moving average hydropathy for each member of the fifth array in accordance with $$b_{j,i} = \left( \sum_k h'_{j,k}(O_{j,k}) \right)/r$$

wherein
K is (i−S) to (i+S),
i is greater than S and up to or equal to (n−S), j is 1 to the total number of sequence in the fifth array,
S is $(r-1)/2$,
r is an odd numeral up to or equal to n, and peptide sequence or fragment thereof;

(XIV) storing said second average hydropathy values in the computer as a seventh array;

(XV) generating within the computer one hydropathic complementary score $\theta_j$ for each anti-peptide sequence or fragment thereof in the fifth array in accordance with $$\theta_j = ((\Sigma (a_k + b_{j,k})^2)/(n-2S))^{1/2},$$

wherein
K is $(S+1)$ to $(n-S)$, and
n and S are as defined above;

(XVI) storing within the computer the hydropathic complementary scores as an eighth array;

(XVII) identifying within the eighth array a group having a lowest score;

(XVIII) identifying and selecting the at least one anti-sense sequence in the fifth array which corresponds to said at least one lowest score and identifying it as the at least one anti-peptide sequence having high affinity and selectivity for the target peptide or fragment thereof (2) synthesizing an anti-polypeptide comprising said anti-peptide sequence; and (3) contacting said anti-polypeptide with a sample comprising said second polypeptide to promote binding therebetween to thereby prevent or reduce the binding of said second polypeptide to said first polypeptide in the presence thereof.

11. The method of claim 10, wherein
said at least one anti-peptide comprises L-amino acids.

12. The method of claim 10, wherein
said at least one anti-peptide comprises D-amino acids.

13. The method of claim 10, wherein
the anti-polypeptide of step (2) consists essentially of the anti-peptide.

14. A method of assaying for a target peptide or a fragment thereof, comprising
(1) designing an anti-peptide sequence having affinity for a target peptide or a fragment thereof contained in the polypeptide by
(I) obtaining an amino acid sequence $P_i$ of the target peptide or a fragment thereof $$P_i = P_1 - P_2 - P_3 - \ldots - P_h;$$

(II) entering into a computer said amino acid sequence as a first array;

(III) obtaining from a first data base a first hydropathic value for each member of the first array $$h_1 - h_2 - h_3 - \ldots - h_n;$$

(IV) storing within the computer said first hydropathic values as a second array;

(V) summing the values in said second array to obtain a value $a_i$ for a first moving average hydropathy $a_i$ for each member of the first array in accordance with $$a_i = \left( \sum_k h_k(P_k) \right)/r$$

wherein
k is $(i-S)$ to $(i+S)$,
i is greater than S and up to or equal to $(n-S)$,
S is $(r-1)/2$,
r is an odd numeral of amino acids in the sequence or fragment thereof;
n is the number of amino acids in the sequence or fragment thereof;

(VI) storing said values for the first moving average hydropathy in the computer as a third array;

(VII) obtaining from a second anti-sense or hydropathically complementary amino acid data base a set comprising at least one anti-sense amino acid per member of the first array;

(VIII) storing within the computer said sets of at least one anti-sense amino acid as a fourth array;

(IX) generating with the computer at least one anti-sense amino acid sequence by selecting one member $Q_{j,i}$ per set in the fourth array $$Q_{j,i} = Q_{j,1} - Q_{j,2} - Q_{j,3} - \ldots - Q_{j,n};$$

(X) storing within the computer said at least one anti-sense amino acid sequence as a fifth array;

(XI) obtaining from the first data base a second hydropathic value $h_{j,i}$ for each member of the fifth array $$h'_{j,i} - h'_{j,2} - h'_{j,3} - \ldots - h'_{j,n}{}';$$

(XII) storing within the computer said second hydropathic values as a sixth array;

(XIII) summing the values in said sixth array to obtain a value $b_{j,i}$ for a second moving average hydropathy for each member of the fifth array in accordance with $$b_{j,i} = \left( \sum_k h'_{j,k}(O_{j,k}) \right)/r$$

wherein
K is $(i-S)$ to $(i+S)$,
i is greater than S and up to or equal to $(n-S)$,
j is 1 to the total number of sequences in the fifth array,
S is $(r-1)/2$,
r is an odd numeral up to or equal to n, and
n is the number of amino acids in the anti-peptide sequence or fragment thereof;

(XIV) storing said second average hydropathy values in the computer as a seventh array;

(XV) generating within the computer one hydropathic complementary score $\theta_j$ for each anti-peptide sequence or fragment thereof in the fifth array in accordance with $$\theta_j = ((\Sigma (a_k + b_{j,k})^2)/(n-2S))^{1/2},$$

wherein
K is $(s+1)$ to $(n-S)$, and
n and S are as defined above;

(XVI) storing within the computer the hydropathic complementary scores as an eighth array;
(XVII) identifying within the eighth array a group having a lowest score;
(VIII) identifying and selecting the at least one anti-sense sequence in the fifth array which corresponds to said at least one lowest score and identifying it as the at least one anti-peptide sequence having high affinity and selectivity for the target peptide or fragment thereof
(2) synthesizing an anti-polypeptide comprising the anti-peptide sequence;
(3) contacting said anti-polypeptide with a sample comprising the target polypeptide to promote binding; and
(4) determining the presence of said polypeptide-bound antipolypeptide.

15. The method of claim 14, wherein said anti-polypeptide is labeled.

16. The method of claim 14, wherein said anti-polypeptide is bound to a solid carrier.

17. The method of claim 14, wherein said at least one anti-peptide comprises L-amino acids.

18. The method of claim 14, wherein said at least one anti-peptide comprises D-amino acids.

19. The method of claim 14, wherein the anti-polypeptide of step (2) consists essentially of the anti-peptide.

20. The method of claim 14, wherein step (4) is conducted by
   (a) designing an anti-(anti-polypeptide) sequence having affinity for said anti-polypeptide or a fragment thereof by the above computer operated method;
   (b) synthesizing second anti-anti-polypeptide comprising said first anti-(anti-polypeptide) sequence;
   (c) labeling said second anti-anti-polypeptide;
   (d) contacting said labeled anti-anti-polypeptide with said sample comprising said polypeptide-bound anti-polypeptide to promote binding therebetween;
   (e) separating said (polypeptide-anti-polypeptide)-bound labeled anti-anti-polypeptide; and
   (f) determining the presence or amount of label present.

21. The method of claim 20, wherein the anti-anti-polypeptide is radiolabeled.

22. A method of synthesizing an anti-peptide macromolecule having affinity for a target peptide or a fragment thereof, comprising
(1) designing an anti-peptide sequence having high affinity and specificity for a target peptide or a fragment thereof contained in the polypeptide by
(I) obtaining an amino acid sequence $P_i$ of the target peptide or a fragment thereof $$P_i = P_1 - P_2 - P_3 - \ldots - P_h;$$

(II) entering into a computer said amino acid sequence as a first array;
(III) obtaining from a first data base a first hydropathic value for each member of the first array $$h_1 - h_2 - h_3 - \ldots - h_n;$$

(IV) storing within the computer said first hydropathic values as a second array;
(V) summing the values in said second array to obtain a value $a_i$ for a first moving average hydropathy $a_i$ for each member of the first array in accordance with $$a_i = \left( \sum_k h_k(P_k) \right)/r$$

wherein
k is $(i-S)$ to $(i+S)$,
i is greater than S and up to or equal to $(n-S)$, S is $(r-1)/2$,
r is an odd numeral up to or equal to n, and
n is the number of amino acids in the sequence or fragment thereof;
(VI) storing said values for the first moving average hydropathy in the computer as a third array;
(VII) obtaining from a second anti-sense or hydropathically complementary amino acid data base a set comprising at least one anti-sense amino acid per member of the first array;
(VIII) storing within the computer said sets of at least one anti-sense amino acid as a fourth array;
(IX) generating with the computer at least one anti-sense amino acid sequence by selecting one member $Q_{j,i}$ per set in the fourth array $$Q_{j,i} = Q_{j,1} - Q_{j,2} - Q_{j,3} - \ldots - Q_{j,n'};$$

(X) storing within the computer said at least one anti-sense amino acid sequence as a fifth array;
(XI) obtaining from the first data base a second hydropathic value $h'_{j,i}$ for each member of the fifth array $$h'_{j,i} - h'_{j,2} - h'_{j,3} - \ldots - h'_{j,n'};$$

(XII) storing within the computer said second hydropathic values as a sixth array;
(XIII) summing the values in said sixth array to obtain a value $b_{j,i}$ for a second moving average hydropathy for each member of the fifth array in accordance with $$b_{j,i} = \left( \sum_k h'_{j,k}(O_{j,k}) \right)/r$$

wherein
K is $(i-S)$ to $(i+S)$,
i is greater than S and up to or equal to $(n-S)$,
j is 1 to the total number of sequences in the fifth array,
S is $(r-1)/2$,
r is an odd numeral up to or equal to n, and
n is the number of amino acids in the anti-peptide sequence or fragment thereof;
(XV) generating within the computer one hydropathic complementary score $\theta_j$ for each anti-peptide sequence or fragment thereof in the fifth array in accordance with $$\theta_j = ((\Sigma (a_k + b_{j,k})^2)/(n-2S))^{1/2},$$

wherein
K is $(S+1)$ to $(n-S)$, and
n and S are as defined above;

(XVI) storing within the computer the hydropathic complementary scores as an eighth array;
(XVII) identifying within the eighth array a group having a lowest score;
(XVIII) identifying and selecting the at least one anti-sense sequence in the fifth array which corresponds to said at least one lowest score and identifying it as the at least one anti-peptide sequence having high affinity and selectivity for the target peptide or fragment thereof
(2) synthesizing an anti-polypeptide comprising the anti-peptide sequence;
(3) covalently binding at least two molecules of said anti-polypeptide to obtain said macromolecule.

23. The method of claim 22, wherein
said at least one anti-peptide comprises L-amino acids.

24. The method of claim 22, wherein
said at least one anti-peptide comprises D-amino acids.

25. The method of claim 22, wherein
the anti-polypeptide of step (2) consists essentially of the anti-peptide 26. The method of claim 22, wherein
the first and second moving average hydropathy values are obtained in accordance with the formulas $$a_i = \sum_{k=1}^{n} h_k w_{i,k},$$

and $$b_{j,i} = \sum_{k=1}^{n} h'_{j,k} w_{i,k}$$

wherein
the $w_{i,k}$ values are such that $$\sum_{k=1}^{n} w_{i,k} = 1$$

for all values of i varying between i and n.

27. The method of claim 22, further comprising
assigning said at least one anti-peptide sequence selected in step XVIII an affinity value, wherein a highest affinity value is assigned the anti-peptide and the lowest affinity and selectivity value to a anti-peptide having a highest score of the group.

28. The method of claim 22, wherein computer in step II by means of a keyboard.

29. The method of claim 22, further comprising
printing said at least one anti-peptide sequence selected in step XVIII.

30. The method of claim 22, wherein the group of lowest hydropathic complementary scores identified in step XVII comprises a range of 1 to 1,000 scores; and the number of anti-peptides identified and selected in step XVIII is in a range of 1 to 1,000.

* * * * *